(12) United States Patent
Singhi et al.

(10) Patent No.: US 12,702,731 B2
(45) Date of Patent: Aug. 11, 2026

(54) UHMWPE DIP-COATED TUBES

(71) Applicant: ZEUS COMPANY INC., Orangeburg, SC (US)

(72) Inventors: Bhavya Singhi, Columbia, SC (US); John Richard Campanelli, West Columbia, SC (US)

(73) Assignee: ZEUS COMPANY INC., Orangeburg, SC (US)

( * ) Notice: Subject to any disclaimer, the term of this patent is extended or adjusted under 35 U.S.C. 154(b) by 388 days.

(21) Appl. No.: 17/896,230

(22) Filed: Aug. 26, 2022

(65) Prior Publication Data

US 2024/0066186 A1 Feb. 29, 2024

(51) Int. Cl.

| | |
|---|---|
| ***A61L 29/08*** | (2006.01) |
| ***A61L 29/14*** | (2006.01) |
| ***A61M 25/00*** | (2006.01) |
| ***A61M 39/02*** | (2006.01) |

(52) U.S. Cl.

CPC ............. *A61L 29/085* (2013.01); *A61L 29/14* (2013.01); *A61M 25/0009* (2013.01); *A61M 39/0247* (2013.01); *A61M 2025/0047* (2013.01); *A61M 2039/0258* (2013.01); *A61M 2039/0279* (2013.01)

(58) Field of Classification Search

CPC ............................... A61L 29/085; A61L 29/14

See application file for complete search history.

(56) References Cited

U.S. PATENT DOCUMENTS

| | | | | |
|---|---|---|---|---|
| 5,070,597 | A | 12/1991 | Holt et al. | |
| 6,602,224 | B1 * | 8/2003 | Simhambhatla ........ | A61L 27/16 428/36.9 |
| 2003/0062650 | A1 * | 4/2003 | Martakos .................. | A61F 2/06 264/209.3 |
| 2009/0312832 | A1 * | 12/2009 | Delap ..................... | A61F 2/966 623/1.2 |
| 2010/0178503 | A1 * | 7/2010 | Tam ........................ | C08L 23/06 264/210.8 |
| 2010/0331883 | A1 * | 12/2010 | Schmitz ......... | A61B 17/320758 606/279 |

(Continued)

FOREIGN PATENT DOCUMENTS

| | | |
|---|---|---|
| WO | WO 2015/194645 A1 | 12/2015 |
| WO | WO 2020/195656 A1 | 10/2020 |

OTHER PUBLICATIONS

NIST SRM 8456 Ultra-High Molecular Weight Polyethylene as a Reference Material for Dynamic Mechanical Analysis ; Roger L. Blaine, PhD (Year: 2005).*

(Continued)

*Primary Examiner* — Erin Mcgrath

(74) *Attorney, Agent, or Firm* — WOMBLE BOND DICKINSON (US) LLP; Jessica L. Gorczynski

(57) ABSTRACT

The disclosure provides tubes comprising ultra high molecular weight poly(ethylene) (UHMWPE). Such tubes can have thin walls and be suitable for applications, e.g., as catheter liners. Methods for preparing such tubes include dip coating a core into a dispersion comprising the UHMWPE, where the dispersion advantageously further comprises an eco-friendly solvent and can optionally include one or more additional components (e.g., fillers and/or other polymers).

20 Claims, 8 Drawing Sheets

(56) References Cited

U.S. PATENT DOCUMENTS

2020/0406011 A1* 12/2020 Rule .................... B32B 27/308
2021/0213175 A1* 7/2021 Sellers ................. A61L 29/041

OTHER PUBLICATIONS

Effect of surface roughness and process parameters on mechanical properties of fabricated medical catheters, B Clemend Bovas et al 2019 Mater. Res. Express 6 125420 (Year: 2019).*
PCT Search Report & Written Opinion dated Feb. 16, 2023 which issued in corresponding PCT Application No. PCT/US2022/042483.
The effect of crystallinity on the mechanical properties and the limiting PV (pressure x velocity) value of PTFE—Triboloty International—pp. 1-10—Sep. 16, 2015.
Whitehand, Garry; The Effects of Orientation in Injection Moulding; Qenos White Paper, Oct. 2015.
Lamberti, G., et al; Modelling of Orientation Evolution in the Film Casting Process; Conference Paper, Aug. 2000.

* cited by examiner

UHMWPE DIP-COATED TUBES

FIELD OF THE INVENTION

The present application relates generally to the field of tubes, such as for use as thin wall catheter liners, comprising Ultra High Molecular Weight Poly(ethylene) (UHMWPE) and to methods relating to such tubes.

BACKGROUND OF THE INVENTION

Vascular therapy uses minimally invasive, catheter-based procedures and specialized equipment and techniques. Catheters used in these procedures commonly employ a coating or liner on the inner wall to provide a lubricious inner surface. A lubricious inside diameter (ID) associated with these devices is beneficial in reducing friction against various catheter technologies such as stents, balloons, atherectomy or thrombectomy devices as they are pushed through the tight confines of the catheter lumen. If the catheter ID is not of sufficient lubricity, devices such as stents can cause the liner to collapse in an accordion-like manner as the devices are pushed through the catheter lumen. The effect of increased lubricity of the catheter ID is a reduced deployment force of catheter devices as they are passed through the lumen, increasing the likelihood of a successful procedure. The mechanical properties of a catheter liner are also extremely important. For example, high tensile and yield strength may be required when certain devices (e.g., flow diversion tubes, embolization, aneurysm bridging, and scaffolding and thrombectomy devices) are passed through microcatheters in a compressed state. The compressed shape exerts an outward radial force, which causes friction with the ID, commonly making delivery of the device through the lumen difficult. On the other hand, high flexibility of a liner is often desirable when catheters must pass through vasculature that involves sharp twists and turns (e.g., cerebral vasculature and below-the-knee (BTK) applications).

Among the various materials that have been pursued as inner wall (base liner) materials for use, e.g., within such catheter devices is polytetrafluoroethylene (PTFE) due to its excellent chemical resistance, high temperature resistance, biocompatibility and very low coefficient of friction/high lubricity. One major drawback of PTFE is that it is not radiation stable. Radiation sterilization (i.e., gamma rays or electron beams) is one of the most widely used and safe sterilization process for medical devices. Radiation sterilization improves the manufacturability of catheters as it can be quickly performed in the manufacturing line, while the ethylene oxide gas sterilization (ETO) procedure, typically used with PTFE-lined catheters, requires storage for up to 48 hours to allow the gas to diffuse out of the sterilized equipment. Also, ETO gas requires careful handling because of its flammability and toxicity. Strict handling requirements and a technically complex sterilization process makes ETO sterilization technique often undesirable. In recent times, medical regulatory organizations worldwide have also been encouraging the medical industry to minimize or replace the use of ETO with alternative sterilization methods.

While several other polymers can withstand gamma irradiation, none can match the lubricity or low coefficient of friction of PTFE. Ultra high molecular weight polyethylene (UHMWPE) comes close to doing so. UHMWPE is a linear polymer with a repeating unit of—$CH_2$—$CH_2$—. Medical grade UHMWPE has long chains with a molecular mass greater than $1\times10^6$ g/mol and is a semi-crystalline polymer. UHMWPE has very low coefficient of friction, excellent wear resistance, good toughness, high impact strength, high resistance to corrosive chemicals, excellent biocompatibility, and low cost. Furthermore, UHMWPE has low processing temperatures, so it can be easily bonded to a variety of other polymeric catheter components. UHMWPE has been used clinically in joint implants for over 40 years, particularly as an articular liner in total hip replacements and tibial insert in total knee replacements. One drawback of UHMWPE is its very high viscosity due to its extremely high molecular weight. UHMWPE does not flow like lower MW polyethylenes or traditional melt processable polymers when raised above its melting temperature. For this reason, many thermoplastic processing techniques, such as injection molding, screw extrusion or blow molding, are not practical for UHMWPE. For the same reason few practical processing techniques are currently available to produce very thin wall tubing that is essential for catheter liners.

Gel spinning process is widely used to process UHMWPE into high strength oriented polyolefin fiber which can be used to make articles such as ropes, tennis strings, fishing nets, filters, anti-ballistic shaped articles, medical textiles and high strength medical sutures. The gel spinning of UHMWPE traditionally involves organic solvents such as decalin, tetralin, toluene, lower alkanes, paraffin oil, mineral oil, paraffin wax, etc., of which decalin and paraffin oil are most widely used. Many of these solvents are often considered unsafe for close contact or environmentally unfriendly. However, gel spinning of UHMWPE has been typically used for producing only fibers and films.

It would be a great benefit to both medical and industrial applications if a radiation sterilizable polymeric material such as UHMWPE could be processed with an eco-friendly solvent into a thin wall tubing, liner or other polymeric structures with good mechanical properties.

SUMMARY OF THE INVENTION

The present disclosure provides UHMWPE tubes produced by dip coating, the tubes exhibiting an average wall thickness less than 0.004 inches (preferably less than 0.002 inches). Advantageously, in some embodiments, such tubes can exhibit low machine direction orientation of the UHMWPE polymer chains (resulting in an intermediate tensile strength and low tensile modulus). Due to the thin walls of the disclosed tubes and the low modulus values of such tubes, they can, in some embodiments, desirably have high flexibility while exhibiting high ID lubricity and abrasion resistance. The combination of properties exhibited by the disclosed tubes, in various embodiments, can render them particularly suitable for use within catheters, including within catheters designed for flexibility, as the thin tube walls and low modulus values of the disclosed tubes provide for a significantly flexible tube/liner product that is also radiation resistant and sterilizable (unlike PTFE liners). In some embodiments, the dip coated tubing can further be oriented in machine and transverse direction to enhance mechanical, thermal and barrier properties. Additionally, the UHMWPE tubes provided herein can, in some embodiments, be used as liners for metallic tubes, like a laser-cut hypotube.

In one aspect is provided an UHMWPE tube comprising: an average wall thickness of 0.001" or less; and a tensile stress at break greater than 9 MPa; and a storage modulus greater than 60 MPa at 37° C. In some embodiments, the tube exhibits a change in the storage modulus between 23° C. and 37° C. of 5 MPa/° C. or less.

In another aspect is provided a UHMWPE layer over a metallic or non-metallic core, wherein: the UHMWPE layer has an average thickness of 0.002" or less; exhibiting an average tensile stress at break greater than 7 MPa and an average storage modulus greater than 150 MPa at 37° C. In certain embodiments, the metallic or non-metallic core and UHMWPE layer are both substantially cylindrical in shape. In some embodiments, the UHMWPE layer over the metallic or non-metallic core comprises a minimum continuous length of 50 ft.

In another aspect is provided a porous/semi-sintered tube having tensile strength greater than 3 MPa at 5% elongation and 5 MPa at 10% elongation and a storage modulus greater than 65 MPa at 37° C.

The solvents and UHMWPE resins used in the dip coating methods can also be used in different concentrations for 3-D printing of polymeric structures/devices/products for various applications.

The invention includes, without limitation, the following embodiments.

Embodiment 1: A tube comprising Ultra High Molecular Weight Poly(Ethylene) (UHMWPE), the tube exhibiting: a. an average wall thickness of 0.004" or less; and b. a tensile stress at break greater than 6 MPa; and c. a storage modulus of greater than 20 MPa at 37° C.

Embodiment 2: The tube of Embodiment 1, wherein at least about 50% by weight of the tube comprises the UHMWPE.

Embodiment 3: The tube of any of Embodiments 1-2, further comprising HDPE and/or LDPE in amounts of less than about 50% by weight, based on a total weight of the tube. Embodiment 4: The tube of any of Embodiments 1-3, further comprising one or more particulate fillers in amounts of less than about 50% by weight, based on a total weight of the tube.

Embodiment 5: The tube of any of Embodiments 1-4, wherein the tube comprises no solvent.

Embodiment 6: The tube of any of Embodiments 1-5, wherein the average wall thickness is 0.0002" to 0.002".

Embodiment 7: The tube of any of Embodiments 1-6, wherein the tube exhibits a change in the storage modulus between 23° C. and 37° C. of 10 MPa/° C. or less.

Embodiment 8: The tube of any of Embodiments 1-7, wherein the tube has an abrasion-resistant inner surface.

Embodiment 9: The tube of any of Embodiments 1-8, wherein the tube has a lubricious inner surface with a coefficient of friction less than 0.2.

Embodiment 10: A coated core, comprising a continuous UHMWPE layer over a core, wherein the UHMWPE layer has an average thickness of about 0.002" or less, an average tensile stress at break greater than 7 MPa and an average storage modulus of greater than 50 MPa at 37° C., when measured after removal from the core.

Embodiment 11: The coated core of Embodiment 10, wherein the core and UHMWPE layer are both substantially cylindrical in shape.

Embodiment 12: The coated core of any of Embodiments 10-11, having a minimum continuous length of 50 ft.

Embodiment 13: The coated core of any of Embodiments 10-12, wherein the core has a contact angle of less than 120 degrees.

Embodiment 14: The coated core of any of Embodiments 10-13, wherein the core has a contact angle of less than 100 degrees.

Embodiment 15: The coated core of any of Embodiments 10-14, wherein the UHMWPE layer exhibits a change in storage modulus between 23° C. and 37° C. of 10 MPa/° C. or less.

Embodiment 16: A tube comprising UHMWPE, prepared by dip coating a core in a dispersion comprising a UHMWPE resin and d-Limonene, wherein the dynamic viscosity of the dispersion is less than 3000 cP at 110° C.

Embodiment 17: The tube of Embodiment 16, wherein the dispersion further comprises one or more other modified polyethylene resins.

Embodiment 18: The tube of any of Embodiments 16-17, wherein the dispersion further comprises one or more particulate fillers.

Embodiment 19: The tube of any of Embodiments 16-18, wherein the dip coating is conducted at a temperature between about 20° C. and about 100'C.

Embodiment 20: A method for preparing a tube comprising UHMWPE, comprising dip coating a core in a dispersion comprising a UHMWPE resin and d-Limonene, wherein the dynamic viscosity of the dispersion is less than 3000 cP at 110° C.

These and other features, aspects, and advantages of the disclosure will be apparent from a reading of the following detailed description together with the accompanying drawings, which are briefly described below. The invention includes any combination of two, three, four, or more of the above-noted embodiments, as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

In order to provide an understanding of the embodiments of the invention, reference is made to the appended drawings, which are not necessarily drawn to scale, and in which reference numerals refer to components of exemplary embodiments of the invention. The drawings are exemplary only, and should not be construed as limiting the invention.

DETAILED DESCRIPTION OF THE INVENTION

Figure 1:
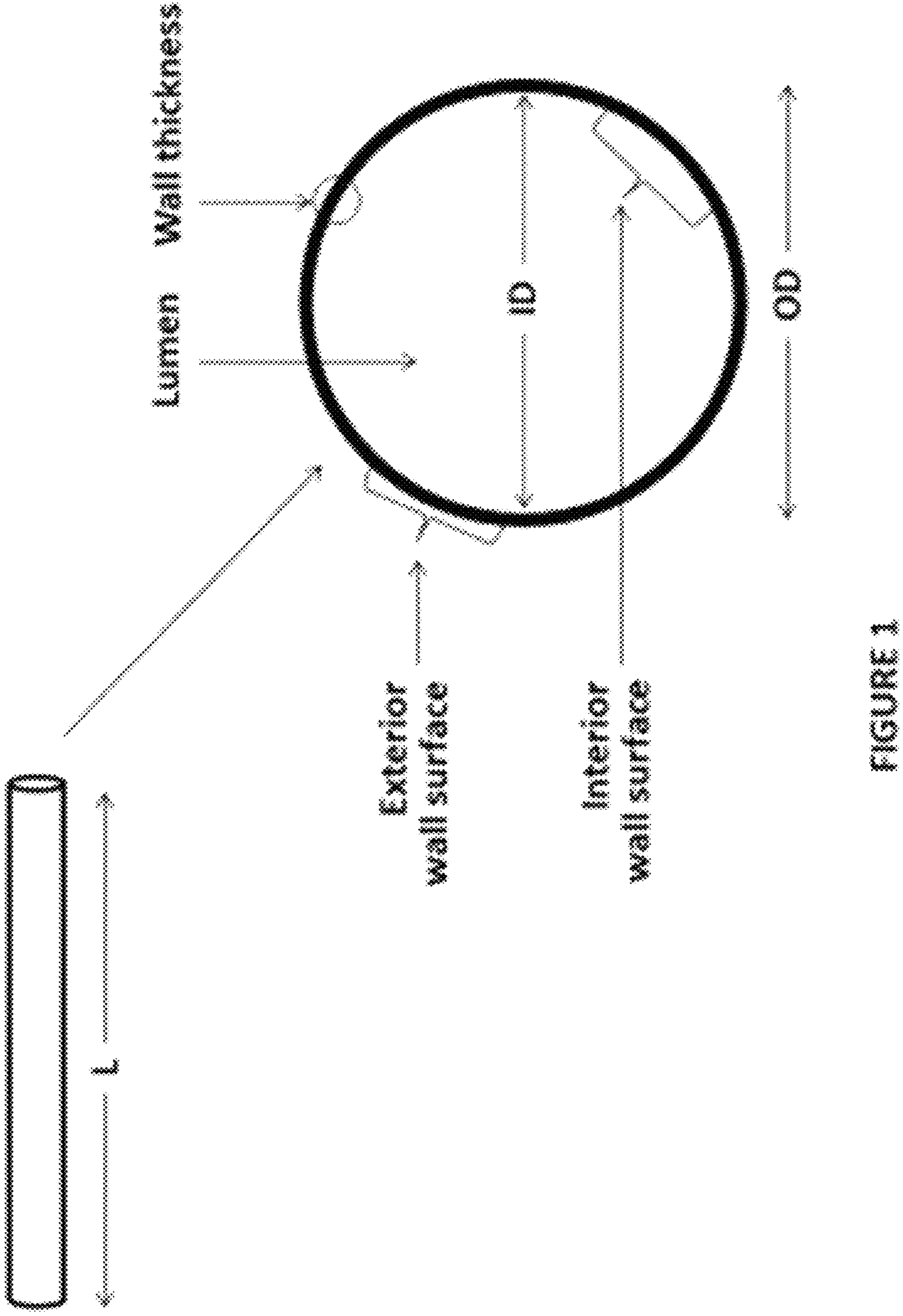
FIG. 1 is a general schematic of a tube of the present disclosure, with relevant parameters, and an expanded schematic of one cross-sectional end face of the tube.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art. As used in this specification and the claims, the singular forms "a," "an," and "the" include plural referents unless the context clearly dictates otherwise.

The present disclosure provides tubes comprising ultra high molecular weight poly(ethylene) (UHMWPE) produced by a dip coating method, with certain physical properties as outlined more fully herein below. By "UHMWPE tubes" is meant that the tubes provided herein comprise, consist essentially of, or consist of UHMWPE. In some embodiments, a majority of the tube (e.g., about 50% by weight or more, about 60% by weight or more, about 70% by weight or more, about 80% by weight or more, about 90% by weight or more, about 95% by weight or more, or about 98% by weight of more) is UHMWPE. Various UHMWPE resins are commercially available and can be used in certain embodiments to provide the UHMWPE tubes described herein.

In certain embodiments, the tubes comprise one or more additional components in addition to the UHMWPE (e.g., fillers such as particulate fillers, or other polymers). For example, in some embodiments, the tubes comprise a tie resin, such as a polyethylene based tie-resin (e.g., including, but not limited to, low-density polyethylene (LDPE), high density polyethylene (HDPE), linear low-density polyethylene (LLDPE), very low density polyethylene (VLDPE), and derivatives, copolymers, and combinations thereof). Further suitable polyethylene-based tie resins include, but are not limited to, anhydride modified polyethylene, ethylene vinyl acetate, ethylene methyl acrylate, ethylene acrylic acid, ethylene methacrylic acid, ethylene-acrylic ester-maleic anhydride terpolymer, and the like. In some embodiments, the tubes consist essentially of UHMWPE and a tie resin and, optionally, a filler. In some embodiments, fillers are particulate fillers. Fillers can be incorporated which may impart specific properties to the tube, such as radiopacity, strength and/or hydrophilicity. In some embodiments, additional polymers can be included within the tubes to impart specific properties such as lubrication, toughness or adhesion. The tubes with added fillers and/or polymers other than UHMWPE may have different properties, such as different mechanical, thermal and barrier properties, different crystallinities, different coefficients of friction, etc.

The UHMWPE tubes provided herein typically do not comprise any appreciable amount of solvent (which may, in some embodiments, be used in the method of preparing the tubes, as will be described more fully herein below). As such, the tubes provided herein can, in some embodiments, be described as comprising less than about 5% by weight, less than about 4% by weight, less than about 3% by weight, less than about 2% by weight, less than about 1% by weight, less than about 0.5% by weight, less than about 0.1% by weight, or less than about 0.05% solvent by weight, based on the total weight of a given tube. In preferred embodiments, the tubes comprise substantially no residual solvent (e.g., less than about 0.01% by weight or less than 0.001% by weight), or no residual solvent (i.e., solvent(s) used in producing such tubes are completely removed). Where any amount of solvent is retained within the tube, it is advantageously an eco-friendly, non-toxic solvent. As such, the tubes provided herein in some embodiments do not comprise any solvent such as decalin, tetralin, toluene, lower alkanes, paraffin oil, mineral oil, or paraffin wax.

A general schematic of a representative tube as provided is shown in FIG. 1. The tube is generally cylindrical in shape. "L" indicates the length of the tube as produced, which can be processed, e.g., cut, to provide tubes of desired length "1" (not shown). As such, the length of the tubes provided herein is not particularly limited. In some embodiments, the length 1 of a tube provided herein is a length suitable for use in a catheter application, e.g., as a liner. For example, in some embodiments, the length 1 is about 6" to about 20", such as about 12" to about 20".

The expanded region at the right of FIG. 1 is a cross-sectional view of the interior of the tube. As shown, the "lumen" is an interior region of the tube, i.e., an open channel/cavity (through which, e.g., a catheter device may be passed). The inner diameter of the tube, shown as "ID" is the average distance from a point on the interior wall of the tube to the opposite/farthest point on the interior wall of the tube. The ID (which determines the diameter of the lumen) can vary and, in some embodiments, is of a size suitable for use in catheter applications, e.g., as a liner. The outer diameter of the tube, shown as "OD" is the average distance from a point on the outer wall of the tube through the lumen of the tube to the opposite/farthest point on the outer wall of the tube. As such, half of the OD value minus the ID value provides the average wall thickness of the tube. A representative "wall thickness," "interior wall surface," and "exterior wall surface" of the tube are also shown in FIG. 1.

In certain embodiments, the present disclosure provides UHMWPE tubes with thin walls. For example, the average wall thickness in some embodiments is less than about 0.004". In some embodiments, the average wall thickness of the disclosed tubes can be about 0.0001" to about 0.004", such as about 0.0002" to about 0.001", about 0.0002" to about 0.002", about 0.0002 to about 0.003", or about 0.0005" to about 0.001."

The wall thickness typically does not vary significantly around the circumference of the tube or along the length (L or 1) of the tube. As such, the wall thickness can generally be described as substantially uniform. The wall tolerance (i.e., the variance from the referenced average wall thickness) in some embodiments can be, for example, +/−0.0002" to +/−0.001" for nominal wall thicknesses of 0.001" to 0.004" or below. In some embodiments, at any given point on a tube provided according to the present disclosure, the wall thickness is less than about 0.001". In some embodiments, at any given point on a tube provided according to the present disclosure, the wall thickness is about 0.0001" to about 0.004", such as about 0.0002" to about 0.001", about 0.0002" to about 0.002", about 0.0002" to about 0.003", or about 0.0002" to about 0.004."

In some embodiments, the UHMWPE tubes provided herein have an abrasion-resistant inner surface. In some embodiments, the UHMWPE tubes provided herein have a lubricious inner surface, e.g., with a coefficient of friction of less than 0.2.

In some embodiments, the tubes provided herein have low storage modulus values, e.g., greater than 50 MPa at 37° C.

Some tubes have higher storage modulus values (e.g., where they have been subjected to secondary processing such as orientation/stretching). Advantageously, in some embodiments, the UHMWPE tubes provided herein have high flexibility, rendering them particularly suitable for certain medical applications, e.g., within catheters as liners (which can be suitably sterilized via radiation). In some embodiments, the tubes exhibit low changes in storage modulus upon heating, e.g., a change in storage modulus between 23° C. and 37° C. of 10 MPa/° C. or less. In certain embodiments, the average tensile stress at break of tubes as provided herein is greater than 7 MPa. In some embodiments, the minimum tensile modulus of tubes as provided herein is about 100 MPa or greater.

In some embodiments, dip coated tubes as provided herein are fully sintered. Such fully sintered tubes generally comprise fully sintered/fused particles and exhibit a continuous, transparent structure. In some embodiments, such dip coated tubes exhibit little to no porosity, as demonstrated in SEM/electronic microscopy images.

When the coated cores are subjected to lower temperatures in the oven (as compared to the annealing/sintering temperature), the tubes produced are generally partially sintered and individual particles are partially fused to form a porous/semi porous structure. At higher temperatures (e.g., near, at, or greater than the sintering temperature), the individual particles generally fully fuse and produce a continuous transparent structure with minimum or no porosity. SEM/Electronic microscopy images support this observation.

In some embodiments, dip coated tubes as provided herein are not fully sintered and can be considered, e.g., semi-sintered. A semi-sintered tube may, due to its microporosity, be more bondable to other materials than a corresponding sintered tube. These semi-sintered tubes may have different mechanical or thermal properties and/or different crystallinity or lubricity as compared to fully sintered/fused continuous structure. Such tubing with porous/semi-porous structure and different mechanical properties can be used for different applications.

The dip coated tubes provided herein generally do not exhibit high machine direction (MD) molecular orientation, as typically exhibited by typical gel spun highly oriented UHMWPE fibers.

In some embodiments, the dip coated tubes provided herein exhibit little to no MD molecular orientation. Orientation in polymer chains is imparted principally in the processing method. Extrusion processes align the chains parallel to the machine direction, but solvent casting/dip-coating does not. One way to distinguish the two is anisotropy of certain physical properties such as modulus in MD and TD.

In some embodiments, the dip coated tube is subjected to a secondary stretching in machine direction (MD) and/or in transverse direction (TD) to impart molecular orientation, alter crystallinity and thereby alter the mechanical, thermal, barrier or electrical/piezo properties in corresponding directions. As such, in some embodiments, dip coated UHMWPE tubes are provided which do exhibit significant MD and/or TD orientation.

The disclosure further provides methods for producing UHMWPE tubes, e.g., tubes exhibiting the chemical and physical properties described herein above. Such methods are generally referred to herein as "dip coating" methods; however, such methods can also, in various embodiments, be characterized as "dispersion coating," "solution coating," or "solvent casting". Dip coating methods for UHMWPE may involve several steps, including: (1) dispersion (or solution) preparation or resin mixing with one or more solvents; (2) dipping/coating; (3) solvent evaporation; (4) sintering/curing; and (5) removal of the core/mandrel, as referenced in further detail below.

First, the dispersion or solution is prepared (e.g., the one or more resins are mixed with one or more solvents). The dispersion or solution generally comprises one or more UHMWPE resins, a solvent, and optionally, any of the additives referenced herein above (e.g., filler(s) and/or tie layer material(s)). It is understood in the following discussion that the term "solvent" can apply to any compound that at least partially solubilizes the UHMWPE resin. It can also be used to refer to dispersant or suspension medium or continuous phase of the dip coating medium. In some embodiments, the mixture of UHMWPE resin and solvent (and, optionally, additional additives) results in a dispersion. In some embodiments, the mixture of UHMWPE resin and solvent (and, optionally, additional additives) results in a solution. The method of combining such components is not particularly limited and various mixing methods and apparatus can be employed.

In some embodiments, the dynamic viscosity of the dispersion used in the disclosed methods is less than about 3000 cP at 110° C.

Non-limiting fine powder UHMWPE resins that are suitable for the dip coating process disclosed herein are typically homopolymeric, usually having a molecular weight greater than $1\times10^6$ g/mol (usually calculated from IV (intrinsic viscosity) measurements). Exemplary resins suitable for this purpose include, but are not limited to, Celanese's [GUR® 2024, GUR® 2122, GUR® 2122-5, GUR® 2126, GUR® 4012, GUR® 4012 F, GUR® 4020-3, GUR® 4022, GUR® 4022-6, GUR® 4032, GUR® 4050-3, GUR® 4056-3, GUR® 4112, GUR® 4113, GUR® 4120, GUR® 4122, GUR® 4122-5, GUR® 4130, GUR® 4150, GUR® 4150-3, GUR® 4152, GUR® 4170, GUR® 4523, GUR® 4550, GUR® 5113, GUR®5129, GUR® 5523, GUR® X161, GUR® X 195, GUR® X204, GUR® X 214, GUR® X217], Mitsui's [Mipelon PM200, XM220, XM221U, XM330], Hi-Zex Million 030S, 145M, 240S, 320MU, 630M, Braskem's UTEC3040, UTEC3041, UTEC4040, UTEC4041, UTEC5540, UTEC5541, UTEC6540, UTEC6540G, UTEC6541, Rochling's Polystone, LyondellBasell's Lupolen UHM 5000, and Asahi Kasei's Sunfine UH.

As noted above, in some embodiments, other additives can be included along with the UHMWPE resin (and incorporated within the tube produced therefrom). For example, polyethylene based tie resins can be included along with the UHMWPE resin(s), such as LDPE, LLDPE, HDPE, VLDPE, anhydride modified polyethylene, ethylene vinyl acetate, ethylene methyl acrylate, ethylene acrylic acid, ethylene methacrylic acid, ethylene-acrylic ester-maleic anhydride terpolymer, and the like.

The dispersion/solution preparation step involves combination of the UHMWPE resin(s) (and optionally, any additional resins and/or other additives) to an appropriate solvent (or a combination of solvents). Solvents typically at least partially dissolve the UHMWPE resin and, in some embodiments, substantially or completely dissolve the UHMWPE resin, e.g., at room temperature or at the temperatures referenced herein (e.g., heat as high as 10° C. less than the melting temperature of the resin). Suitable solvents include, but are not limited to, xylene, cyclohexane, benzene, toluene, carbon tetrachloride, tetrahydrofuran, chloroform, dodecane and other hydrocarbon chains (e.g., with 11 to 16 carbons), naphthalene, p-xylene, 1,2,4-trichlorobenzene, kerosene, camphene, paraffin oil, decalin, polybutene, sunflower oil, palm oil, and/or orange oil (terpene). In some embodiments, an environmentally friendly solvent is used to prepare the solution/dispersion. For example, in some embodiments, a solvent such as D-limonene [CAS number 5989-27-5] can advantageously be employed for the dispersion/solution preparation step. D-limonene is a cyclic terpene found in citrus extract/oil and is also known as limonene or 1-limonene or dl-limonene or (+)-limonene or (+)-dipentene or (+)-(R)-limonene or (R)-4-isopropenyl-1-methyl-1-cyclohexene. In some embodiments, the solvent is primarily limonene, e.g., the solvent contains about 50% or more, about 60% by more, about 70% or more, about 80% or more, about 90% or more, about 95% or more, about 98% or more, or about 99% or more by weight of limonene. In some embodiments, the dispersion or solution provided according to the present disclosure consists essentially of one or more UHMWPE resins, limonene, and optionally, any additional tie layer resins and/or fillers as referenced herein above.

To form a proper dispersion, the polymer resin can be mixed in the solvent through mechanical agitation with or without applying heat (as high as 10° C. less than the melting temperature of the resin). In some embodiments, the disclosed method may further comprise subjecting the dispersion to an optional filtration step to remove large agglomerates. The dispersion or solution is then used to dip coat a component. Typically, the UHMWPE-containing dispersion/suspension is coated over a metallic or non-metallic core/substrate, e.g., including, but not limited to, a wire or mandrel. In some embodiments, the core/substrate can comprise a surface comprising poly(tetrafluoroethylene), filled poly(tetrafluoroethylene), or silver-coated copper. The shape and size and composition of the core/substrate is not particularly limited. In some embodiments, the core/substrate is cylindrical in shape. In some embodiments, the core/substrate is smooth; in other embodiments, the core/substrate is patterned (which can, in some embodiments, lend such patterning to the ID of the resulting tube). It is understood that, in some embodiments, the reference to "UHMWPE" being coated on a core/substrate includes additional components, e.g., tie layer material, filler, solvent, etc.

The UHMWPE coating on the core/substrate generally adheres to the underlying substrate to some extent; the adhesion of the UHMWPE coating to the core/substrate is typically dependent on the relative surface tension of the core/substrate and the UHMWPE coating. One method to measure surface tension of a metallic/non-metallic core/substrate/mandrel is contact angle. An appropriate core/mandrel can, in some embodiments, be selected based on its contact angle values, typically less than 120 degrees, preferably less than 100 degrees. Contact angle values can be evaluated, e.g., as described in U.S. Pat. No. 5,268,733 to Wright et al., which is incorporated herein by reference in its entirety.

The dip coating step can be a batch or continuous process.

In a batch process, a reservoir contains the dispersion or solution. For example, in one embodiment, a mandrel/core is dipped in the dispersion/solution momentarily (while it is in stationary or in rotational mode around its central axis) and pulled out manually or through an automatic process. In some embodiments, the pulled material may go through a sizing die following the dipping to remove excess coating material and to ensure a uniform coating around the circumference. The coated core then is generally heated (e.g., placed in an oven) to dry/devolatilize/drive off the solvent at a set temperature. Suitable temperatures will depend, for example, on the solvent being removed at this stage. The drying/devolatilization oven temperature may vary from 100° C. to 230° C. depending on the boiling point of the solvent that was used to produce the dispersion. Advantageously, the drying/devolatilization results in the removal of substantially all of the solvent. The coated core may, in some embodiments, be subsequently subjected to other (e.g., higher) temperatures for sintering/tempering/melt fusing of polymeric particles or annealing. The sintering oven temperature can be set between 120° C. to 250° C. depending on the molecular weight of the UHMWPE resin or viscosity/flowability of the grade. These steps (i.e., dip coating and heating) can, in some embodiments, be repeated multiple times to increase the coating thickness to the desired value (and, correspondingly, the wall thickness of a tube produced therefrom).

In a continuous coating process, the core is passed through a bath of the dispersion/solution to be coated and then is passed through a sizing die, followed by a devolatilization and sintering and/or heating at higher temperature (e.g., in an oven). Again, in some embodiments, it may be advantageous to further increase the coating thickness; in such embodiments, the coated material exiting the sintering oven can be returned to the same or another coating reservoir in a loop, is passed through a different appropriately sized sizing die and then is again heated (e.g., in the ovens).

The inside surface of a hollow metallic or non-metallic tube can also be coated with the dispersion in a similar method while the hollow tube is in stationary or rotational mode around its axis. If it is intended that the UHMWPE coating be removed and subsequently bonded to another material such as polyimide (PI), polyurethane (PU), nylon or a polyamide ether copolymer (PEBA), or any other polymer or copolymer, then the dispersion can also include a tie resin, including, but not limited to, anhydride modified polyethylene, ethylene vinyl acetate, ethylene methyl acrylate, ethylene acrylic acid, ethylene methacrylic acid, ethylene-acrylic ester-maleic anhydride terpolymer, or other similar resins. The amount of tie layer resin, wherein included, can be up to about 50% by weight of the resin of the dispersion.

As noted above, when the coated cores are subjected to lower temperatures in the oven (as compared to the annealing/sintering temperature), the tubes produced are generally partially sintered and individual particles are partially fused to form a porous/semi porous structure. At higher temperatures (e.g., near, at, or greater than the sintering temperature), the individual particles generally fully fuse and produce a continuous transparent structure with minimum or no porosity. As such, in some embodiments, the physical properties (e.g., mechanical properties, thermal properties, crystallinity properties, lubricity, etc.) can be tailored by selection of suitable temperature(s) for heat treatment.

Once the coated core is out of the oven and cooled (either in air or water quenched), the product can be used as is for further processing, which generally depends on the intended use. For example, in some embodiments, various materials can be added to the outer surface of the coating; in certain embodiments, different metallic/non-metallic fibers can be braided over the outer surface.

In some embodiments, the coating is removed from the underlying core to give a tube, e.g., by stretching the coated core to remove the coating from the core. One, non-limiting method for removal of the coating involves removal of small sections of coating at two distal locations of the coated core, exposing the core section. The two exposed locations can be clamped (e.g., using an Instron tensile machine) and the core can then be stretched. The degree of stretching targeted during this step is usually, for example, at least about 5%, with a maximum stretching percentage of 30% (or until just before the core breaks or the outer diameter of the coated core reduces down enough to break the bond between the coating and the core). After the core is stretched sufficiently, the coating usually slides off easily, in the form of a tube. The removed coating is, advantageously, in the form of a free-standing tube (of length L). This tube can optionally be processed, e.g., by cutting the long tube into shorter lengths 1 as desired, e.g., for certain specific applications.

The coated tube or stand-alone tube can, in some embodiments, be further processed by stretching (for example, 1.1 to 10 times) in the machine direction (with or without application of heat) to impart molecular orientation. Such stretching can serve to increase the tensile strength of the coating/tube and also reduce the wall thickness further. If the coated tube is being stretched, the core can then be separated from the coating, e.g., by the same method described above. The machine direction oriented tube can then optionally be further oriented (with or without application of heat) by stretching, for example, 1.1 to 10 times in the transverse direction (TD) mechanically or pneumatically (e.g. applying air in the ID of the tube). Alternately, an unstretched tube (e.g., after removing the coating from the core) can be oriented simultaneously in the machine and transverse directions (with or without application of heat) mechanically or pneumatically or in a combination (e.g., via a balloon blowing machine). The stretching process can be used for partially sintered and fully sintered tubes to produce different structural and mechanical effects in the tubes. In some embodiments, a partially sintered tube can also be subjected to a post-stretching sintering process to produce a sintered tube, which can have properties different from a corresponding tube that was stretched after being fully sintered.

EXPERIMENTAL

Embodiments of the present disclosure are more fully illustrated by the following examples, which are set forth to illustrate aspects of the present disclosure and are not to be construed as limiting thereof. Unless otherwise noted, all parts and percentages are by weight.

UHMWPE tubes were prepared according to the specific example writeups provided below. A Brookfield Viscometer LVDV II+ Pro was used to map a temperature vs viscosity profile of the various dispersions used in the specific examples. The spindles were used at a 100 rpm setting for all the dispersions and the tests were run from a temperature of 20° C. to at least 10° C. below the melt temperature of the resin, as the dispersion starts to gel up and agglomerate close to the melt temperature of the resin. It is to be noted that suitable dispersions for the preparation of UHMWPE tubes as generally described in the present application are not limited to the specific dispersions in the examples.

An Instron 5965 dual column mechanical tester running Bluehill 3 v3.73.4823 operating software was used to determine the tensile properties of the dip coated UHMWPE tubes. The tests were performed at room temperature at a rate of 20"/min using a 1 kN load cell attached to pneumatic grips with serrated face inserts set to a 2 inch gage length. The average tensile properties are listed in Table 2.

A TA instruments Q800 DMA with the film tension fixture was used to determine the thermo-mechanical properties of the dip coated UHMWPE tube isolated from the core. The main property of interest was storage modulus (E'). A temperature scan was performed from −100° C. to 130° C. with an isothermal hold for five minutes at −100° C. The sample was heated at a constant rate of 3° C./min while being displaced at a constant amplitude of 15 μm with a fixed frequency tensile oscillation of 1 Hz. The resulting DMA data was imported into TA instruments TRIOS software v4.3, and the average storage modulus at 23° C. and 37° C. is listed in Table 2. Built catheters and catheter components such as liners and jackets can be tested using an interventional device testing equipment such as the IDTE3000 from MSI which can measure and record device performance features such as pushability, flexibility, torqueability, etc.

Several dispersions were made with Mipelon™ PM200 UHMWPE resin and d-limonene solvent with varying concentrations between 1% wt./vol. to 100% wt./vol. Dispersions were also made with Microthene FE53200 ethylene vinyl acetate (EVA) and d-limonene solvent with varying concentrations between 1% wt./vol. to 100% wt./vol. Another dispersion was made by adding EVA to a dispersion of UHMWPE and d-Limonene. All dispersions were tested with the Brookfield Viscometer as described above to obtain their temperature vs viscosity profiles, which are shown in FIGS. 2-6.

Example 1

A PTFE mandrel of 0.109" OD was dip coated with Dispersion A at 80° C., followed by devolatilazation of the solvent at 170° C. The partially sintered tube was dip coated with Dispersion G at 50° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 2

A PTFE mandrel of 0.109" OD was dip coated with Dispersion B at 80° C., followed by devolatilazation of the solvent at 170° C. The partially sintered tube was dip coated with Dispersion G at 50° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 3

A PTFE mandrel of 0.109" OD was dip coated with Dispersion C at 10° C., followed by devolatilazation of the solvent at 170° C. The partially sintered tube was dip coated again with Dispersion C at 10° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 4

Figure 7A:
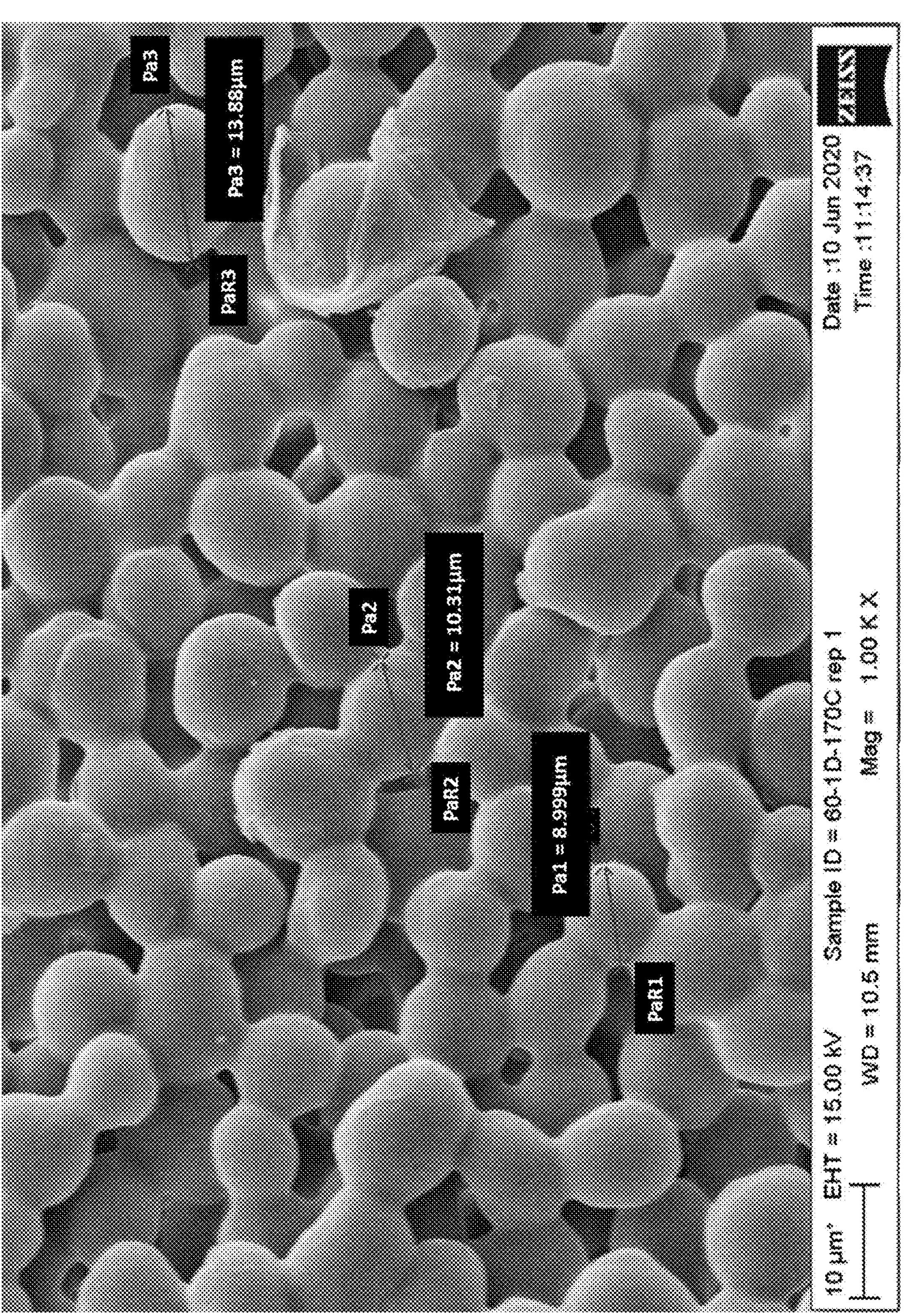
FIG. 7A is a scanning electron microscope (SEM) image of partially-sintered tubing from Example 4.
Figure 7B:
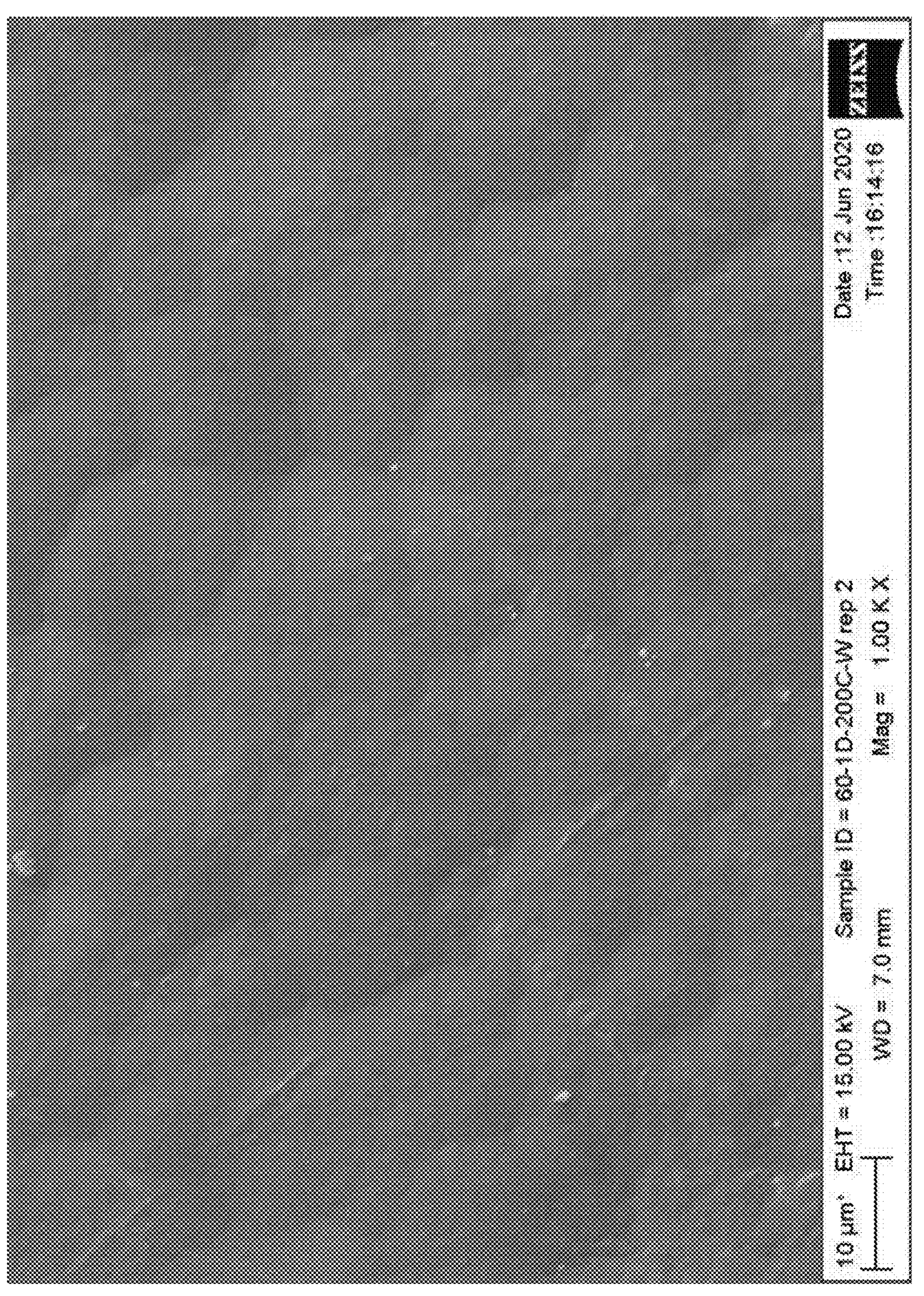
FIG. 7B is a SEM image of fully-sintered tubing from Example 4.

A PTFE mandrel of 0.109" OD was dip coated with Dispersion C at 80° C., followed by devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form. SEM images using a ZEISS EVO 40 at 1000× magnification were taken of this material in partially-sintered form and in fully sintered form are shown in FIGS. 7A and 7B, respectively.

Example 5

A PTFE mandrel of 0.109" OD was dip coated with Dispersion F at 50° C., followed by devolatilazation of the solvent at 130° C. The partially sintered tube was dip coated again with Dispersion F at 50° C., followed by another round of devolatilazation of the solvent at 130° C. The coated tubing was then sintered at 160° C. on the core and quenched in cold water. The core was then stretched as described above and the coating (in tubular form) was removed from the core without deforming or damaging the layer to give a free-standing product in tubular form.

Example 6

A PTFE mandrel of 0.109" OD was dip coated with Dispersion G at 50° C., followed by devolatilazation of the solvent at 150° C. The partially sintered tube was dip coated again with Dispersion G at 50° C., followed by another round of devolatilazation of the solvent at 150° C. The coated tubing was then sintered at 180° C. on the core and quenched in cold water. The core was then stretched as described above and the coating (in tubular form) was removed from the core without deforming or damaging the layer to give a free-standing UHMWPE product in tubular form.

Example 7

A PTFE mandrel of 0.109" OD was dip coated with Dispersion C at 80° C., followed by devolatilazation of the solvent at 170° C. The partially sintered tube was dip coated again with Dispersion E at 50° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 8

A PTFE mandrel of 0.109" OD was dip coated with Dispersion D at 80° C., followed by devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 9

A PTFE mandrel of 0.109" OD was dip coated with Dispersion B at 80° C., followed by devolatilazation of the solvent at 170° C. The partially sintered tube was dip coated again with Dispersion B at 80° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 10

A silver-plated copper (SPC) mandrel of 0.060" OD was dip coated with Dispersion B at 80° C., followed by devolatilazation of the solvent at 170° C. The partially sintered tube was dip coated again with Dispersion B at 80° C., followed by another round of devolatilazation of the solvent at 170° C. The coated tubing was then sintered at 200° C. on the core. Due to the affinity of polyethylene with metal, it was difficult to separate the UHMWPE tube from the SPC mandrel without damaging the tubular form.

Example 11

A textured glass-filled PTFE mandrel of 0.088" OD was dip coated with Dispersion B at 80° C., followed by devolatilazation of the solvent at 170° C. The partially sintered tube was dip coated again with Dispersion B at 80° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 12

A PTFE mandrel of 0.109" OD was dip coated with Dispersion C at 80° C., followed by devolatilazation of the solvent at 170° C. The partially sintered tube was dip coated again with Dispersion C at 80° C., followed by another round of devolatilazation of the solvent at 170° C. The coated tubing was then sintered at 200° C. on the core and quenched in cold water. The core was then stretched as described above and the coating (in tubular form) was removed from the core without deforming or damaging the layer to give a free-standing UHMWPE product in tubular form.

Example 13

The UHMWPE tubing from Example 12 was stretched approximately 300% at 120° C. for improved axial orientation and mechanical properties.

Example 14

A PTFE mandrel of 0.125" OD was dip coated with Dispersion C at 80° C. in a continuous process, followed by devolatilazation of the solvent at 170° C. The partially sintered tube was dip coated again with Dispersion C at 80° C., followed by another round of devolatilazation of the solvent at 170° C. The coated tubing was then sintered at 200° C. on the core and cooled in air. The coated core was then cut into smaller lengths and stretched as described above and the coating (in tubular form) was removed from the core without deforming or damaging the layer to give a free-standing UHMWPE product in tubular form. Approximately 50 ft of mandrel was coated with the dispersion.

TABLE 1

List of Dispersions and Their Components

Figure 2:
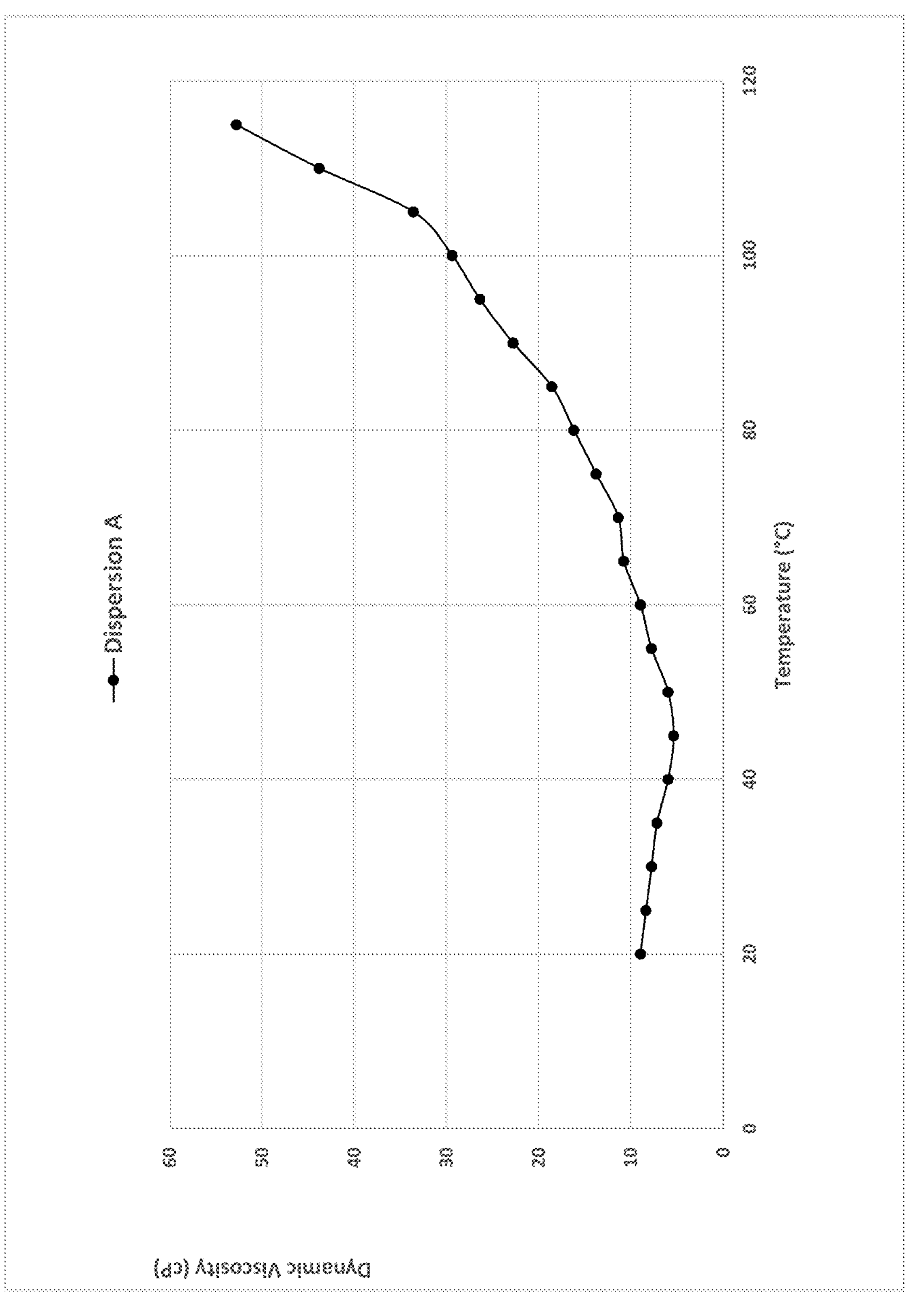
FIG. 2 is a plot of temperature versus viscosity for a dispersion ("A") employed to make certain UHMWPE tubes according to one non-limiting embodiment of the disclosure.
Figure 3:
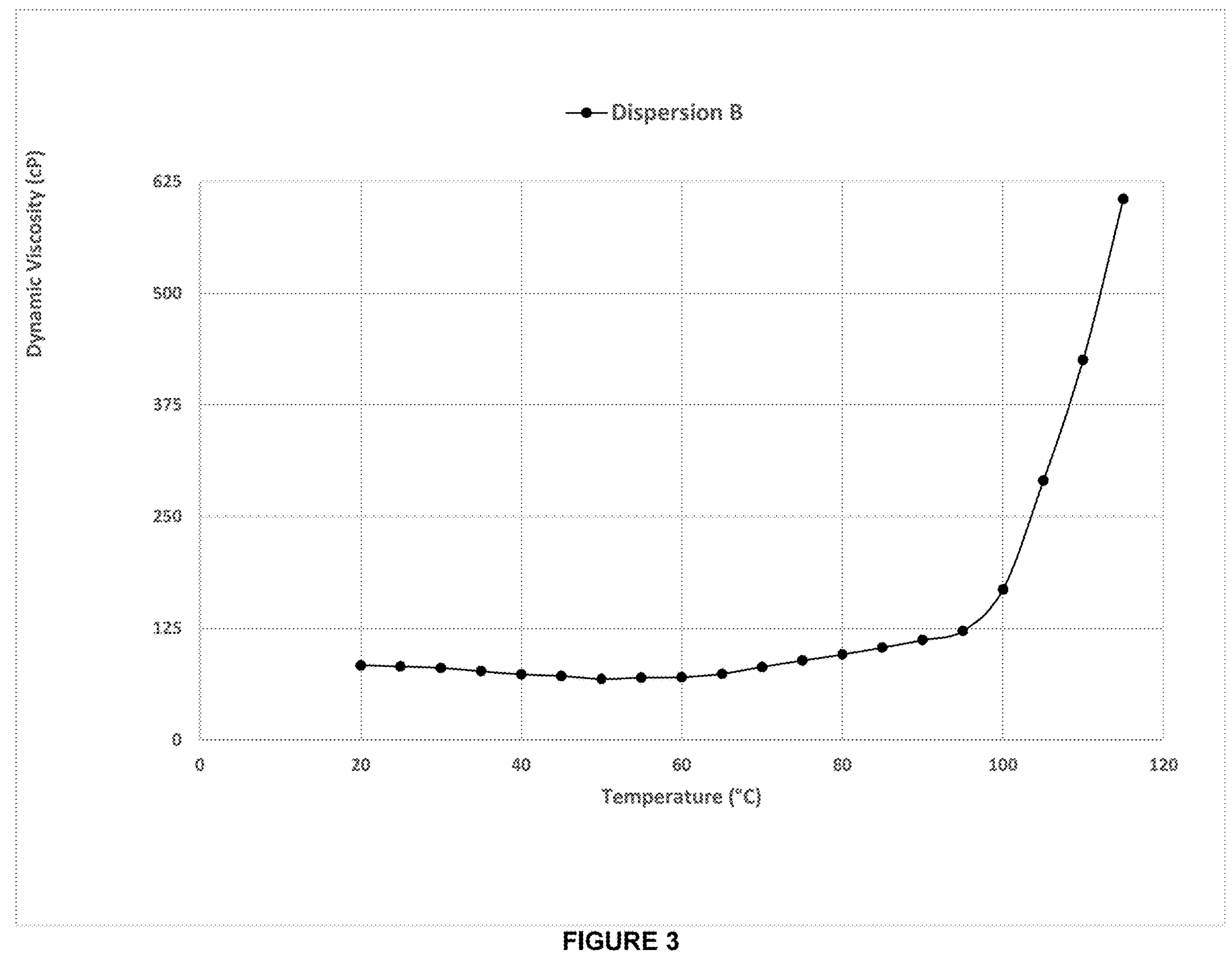
FIG. 3 is a plot of temperature versus viscosity for a dispersion ("B") employed to make certain UHMWPE tubes according to one non-limiting embodiment of the disclosure.
Figure 4:
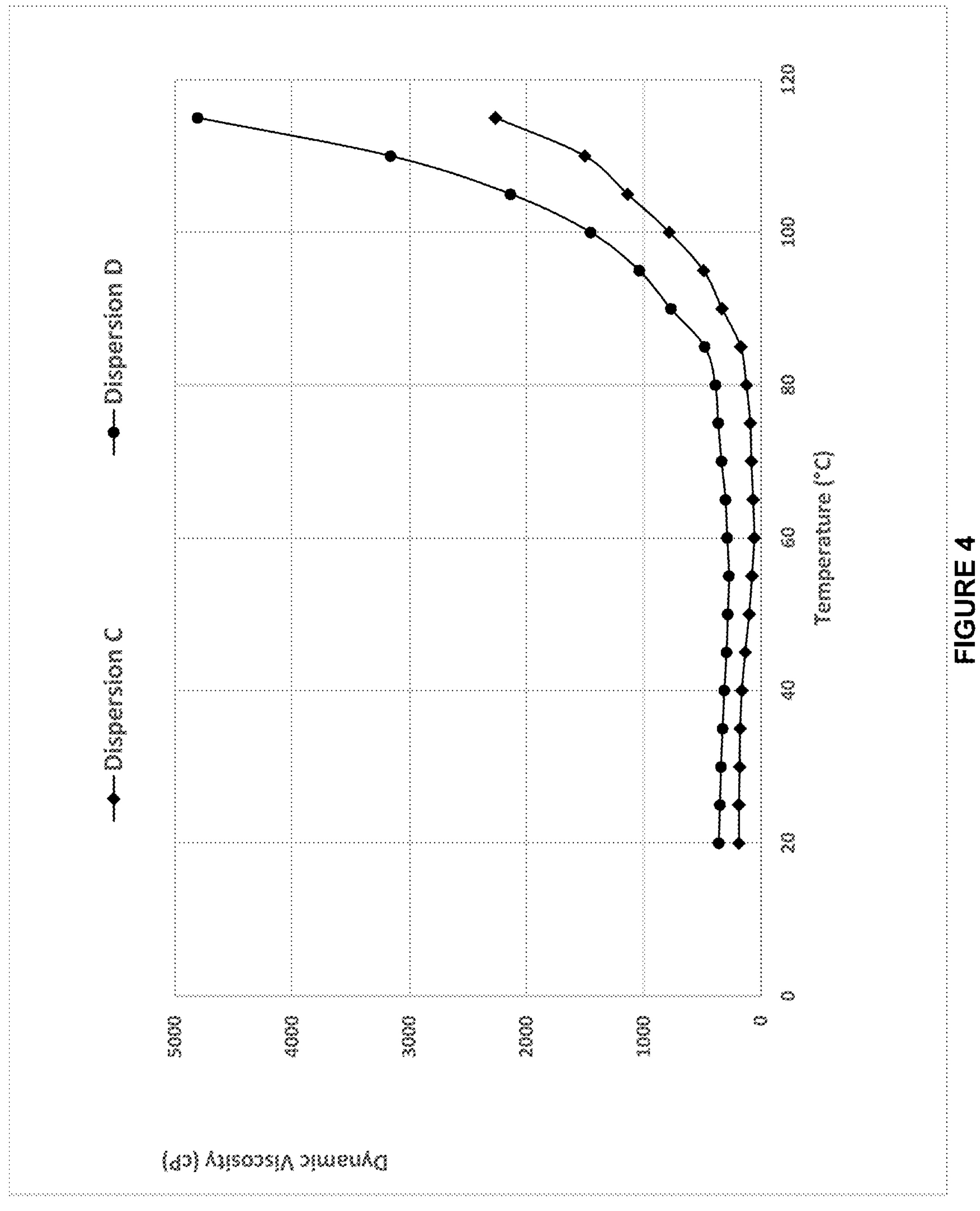
FIG. 4 is a plot of temperature versus viscosity for dispersions ("C" and "D") employed to make certain UHMWPE tubes according to certain non-limiting embodiments of the disclosure.
Figure 5:
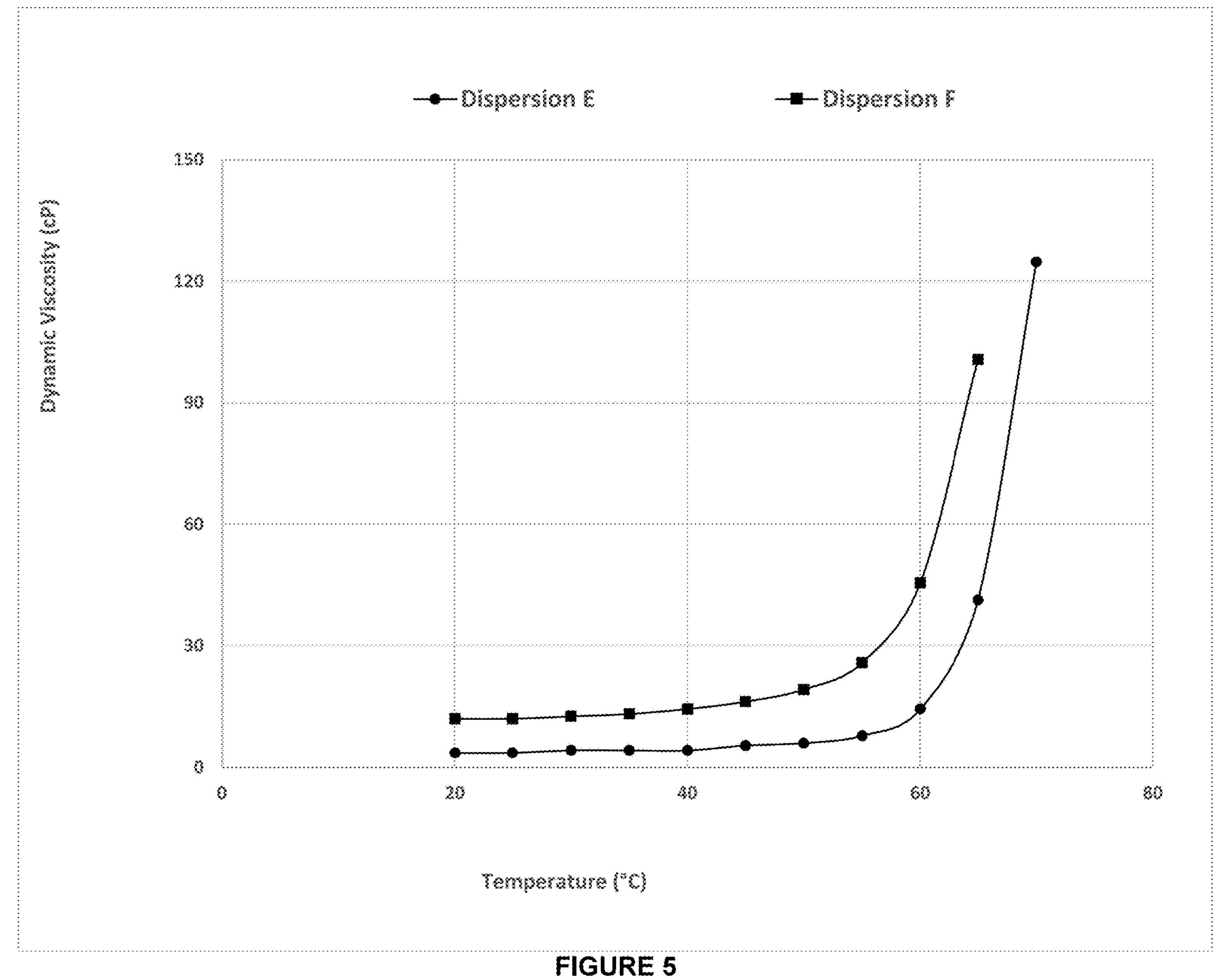
FIG. 5 is a plot of temperature versus viscosity for dispersions ("E" and "F") employed to make certain comparative ethylene vinyl acetate (EVA) tubes.
Figure 6:
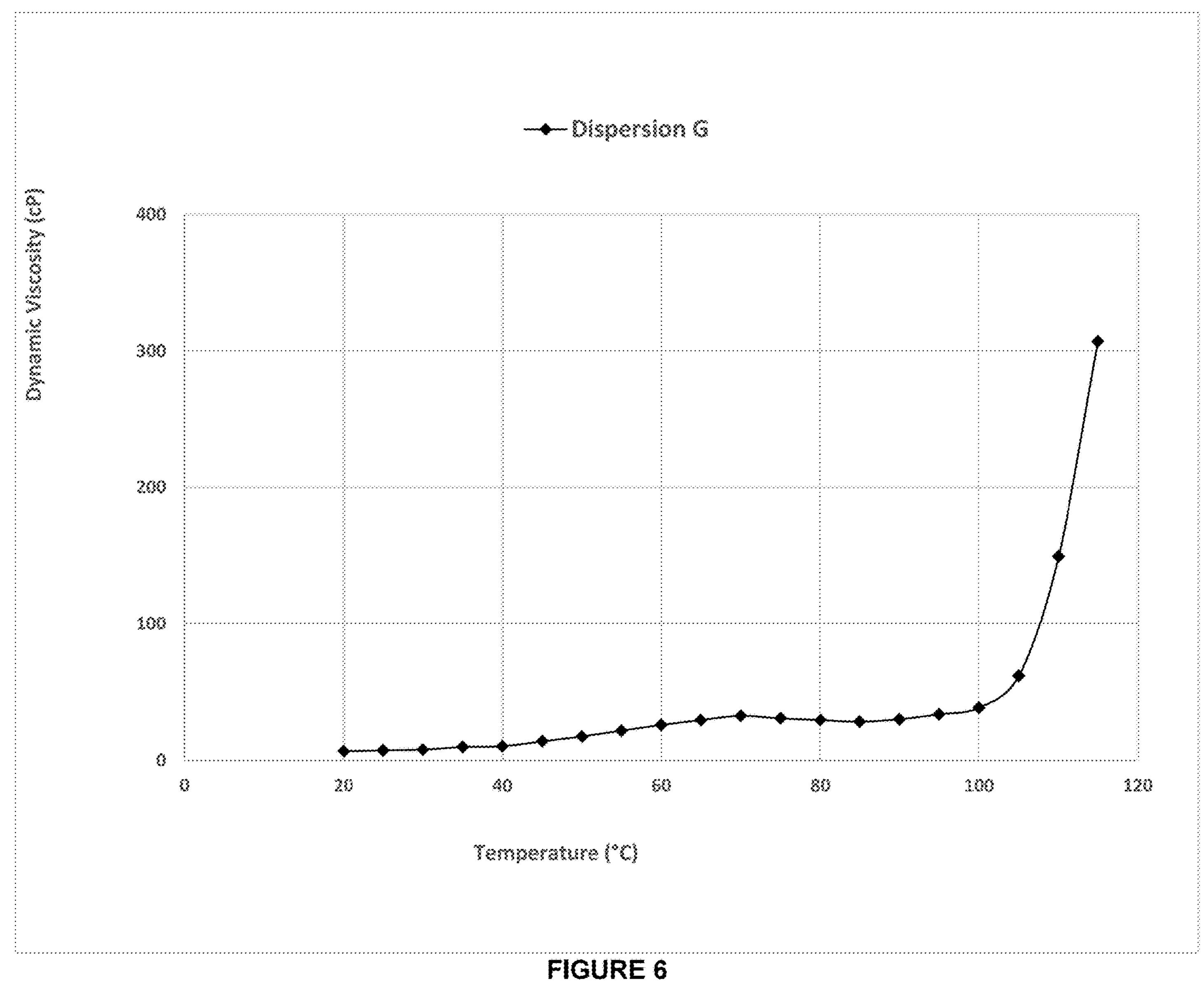
FIG. 6 is a plot of temperature versus viscosity for a dispersion ("G") employed to make certain tubes comprising UHMWPE and EVA according to one non-limiting embodiment of the disclosure.

| Dispersion | Resin | Solvent | Viscosity |
|---|---|---|---|
| A | UHMWPE | d-Limonene | FIG. 2 |
| B | UHMWPE | d-Limonene | FIG. 3 |
| C | UHMWPE | d-Limonene | FIG. 4 (C) |
| D | UHMWPE | d-Limonene | FIG. 4 (D) |
| E | EVA | d-Limonene | FIG. 5 (E) |
| F | EVA | d-Limonene | FIG. 5 (F) |
| G | UHMWPE + EVA | d-Limonene | FIG. 6 |

EVA was used to demonstrate that tie-resin can be added to the dispersion, or that a multi-layered coating can be formed, where one layer is UHMWPE and another is EVA.

TABLE 2

Dimensions and Mechanical Properties

| | Dimensions | | Tensile Properties | | | Storage Modulus | |
|---|---|---|---|---|---|---|---|
| | OD (inch) | Wall Thickness (inch) | Tensile Modulus (MPa) | Stress @ Break (MPa) | Strain @ Break (%) | 23° C. (MPa) | 37° C. (MPa) |
| Ex. 1 | 0.101 | 0.0011 | 153 | 7.9 | 13 | 265 | 168 |
| Ex. 2 | 0.099 | 0.0010 | 131 | 8.1 | 20 | 118 | 76 |
| Ex. 3 | 0.102 | 0.0012 | — | — | — | 435 | 346 |
| Ex. 4 | 0.099 | 0.0006 | — | — | — | 325 | 169 |
| Ex. 5 | 0.104 | 0.0021 | — | — | — | 25 | 19 |
| Ex. 6 | 0.104 | 0.0023 | — | — | — | 162 | 119 |
| Ex. 7 | 0.099 | 0.0008 | 170 | 9.2 | 10 | 111 | 66 |
| Ex. 8 | 0.107 | 0.0051 | — | — | — | 450 | 309 |
| Ex. 9 | 0.101 | 0.0010 | 312 | 8.2 | 6 | 372 | 244 |
| Ex. 10 | 0.064 | 0.0014 | — | — | — | — | — |
| Ex. 11 | 0.091 | 0.0011 | — | — | — | — | — |
| Ex. 12 | 0.105 | 0.0031 | 588 | 10.3 | 88 | 735 | 536 |
| Ex. 13 | 0.066 | 0.0020 | 1100 | 20.5 | 19 | 815 | 646 |
| Ex. 14 | 0.125 | 0.0011 | — | — | — | — | — |

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An Ultra High Molecular Weight Polyethylene (UHMWPE) tube,
 wherein the tube comprises distinct, partially fused UHMWPE particles,
 wherein the tube exhibits:
 a. an average wall thickness of 0.004" or less; and
 b. a tensile stress at break greater than 6 MPa, and
 wherein the tube is formed by dip coating such that the tube exhibits little to no machine direction molecular orientation.

2. The UHMWPE tube of claim 1, wherein at least about 50% by weight of the tube comprises the UHMWPE.

3. The UHMWPE tube of claim 1, further comprising high density polyethylene (HDPE) and/or low density polyethylene (LDPE) in amounts of less than about 50% by weight, based on a total weight of the UHMWPE tube.

4. The UHMWPE tube of claim 1, further comprising one or more particulate fillers in amounts of less than about 50% by weight, based on a total weight of the UHMWPE tube.

5. The UHMWPE tube of claim 1, wherein the UHMWPE tube comprises no solvent.

6. The UHMWPE tube of claim 1, wherein the average wall thickness is 0.0002" to 0.002".

7. The UHMWPE tube of claim 1, wherein the UHMWPE tube exhibits a change in storage modulus between 23° C. and 37° C. of 10 MPa/° C. or less.

8. The UHMWPE tube of claim 1, wherein the UHMWPE tube has an abrasion-resistant inner surface.

9. The UHMWPE tube of claim 1, wherein the UHMWPE tube has a lubricious inner surface with a coefficient of friction less than 0.2.

10. A catheter comprising the UHMWPE tube of claim 1.

11. The catheter of claim 10, wherein the catheter is sterilized.

12. The UHMWPE tube of claim 1, wherein the UHMWPE tube is porous.

13. A coated core, comprising a continuous Ultra High Molecular Weight Polyethylene (UHMWPE) layer in the form of a tube over a core,
 wherein the UHMWPE layer comprises distinct, partially fused UHMWPE particles,
 wherein the UHMWPE layer has an average thickness of about 0.002" or less, and an average tensile stress at break greater than 6 MPa, when measured after removal from the core, and
 wherein the UHMWPE layer is formed by dip coating such that the UHMWPE layer exhibits little to no machine direction molecular orientation.

14. The coated core of claim 13, wherein the core and UHMWPE layer are both substantially cylindrical in shape.

15. The coated core of claim 13, having a minimum continuous length of 50 ft.

16. The coated core of claim 13, wherein the core has a contact angle of less than 120 degrees.

17. The coated core of claim 13, wherein the core has a contact angle of less than 100 degrees.

18. The coated core of claim 13, wherein the UHMWPE layer exhibits a change in storage modulus between 23° C. and 37° C. of 10 MPa/° C. or less.

19. An Ultra High Molecular Weight Polyethylene (UHMWPE) catheter liner, the catheter liner in the form of a tube exhibiting:

a. an average wall thickness of 0.004" or less; and b. a tensile stress at break greater than 6 MPa, wherein the UHMWPE catheter liner comprises distinct, partially fused UHMWPE particles, and wherein the UMHWPE catheter liner is formed by dip coating such that the tube exhibits little to no machine direction molecular orientation.

20. The UHMWPE catheter liner of claim 19, wherein the UHMWPE catheter liner is porous.

* * * * *